(12) United States Patent
Ishikawa et al.

(10) Patent No.: US 6,417,175 B1
(45) Date of Patent: Jul. 9, 2002

(54) PHOSPHONOCEPHEM DERIVATIVES, PROCESS FOR THE PREPARATION OF THE SAME, AND USE THEREOF

(75) Inventors: Tomoyasu Ishikawa, Otsu; Shohei Hashiguchi, Toyonaka; Yuji Iizawa, Muko, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/555,949

(22) PCT Filed: Dec. 17, 1998

(86) PCT No.: PCT/JP98/05709
§ 371 (c)(1),
(2), (4) Date: Jun. 6, 2000

(87) PCT Pub. No.: WO99/32497
PCT Pub. Date: Jul. 1, 1999

(30) Foreign Application Priority Data

Dec. 19, 1997 (JP) ................................. 9-351499

(51) Int. Cl.$^7$ .................... C07D 9/6561; A61K 31/675
(52) U.S. Cl. .................... 514/80; 540/225; 540/227
(58) Field of Search ................. 540/227, 225; 514/80

(56) References Cited

U.S. PATENT DOCUMENTS

| 4,145,540 A | 3/1979 | Ochiai et al. |
| 4,268,509 A | 5/1981 | Teraji et al. ................. 544/22 |
| 4,503,220 A | 3/1985 | Farge et al. |
| 4,563,449 A | 1/1986 | Teraji et al. ................. 514/203 |

FOREIGN PATENT DOCUMENTS

| EP | 0 007 470 | 2/1980 |
| EP | 0 099 553 | 2/1984 |
| JP | 55-11600 | 1/1980 |
| JP | 59-31791 | 2/1984 |
| JP | 9-100283 | 4/1997 |
| JP | 9-100287 | 4/1997 |

OTHER PUBLICATIONS

Translation of JP 9–100283 (1997).*
Abstract for JP 10–265488 (1998).
Abstract for JP 9–100283 (1996).
Abstract for JP 62–238291 (1986.

* cited by examiner

*Primary Examiner*—Mark L. Berch
(74) *Attorney, Agent, or Firm*—Mark Chao; Elaine M. Ramesh

(57) ABSTRACT

A novel cephem compound of the formula:

wherein $R^1$ is a phosphono group or a group convertible to a phosphono group; $R^2$ is a hydrogen atom or a group having a linkage through a carbon atom; each of Q and X is a nitrogen atom or CH; Y is S, O or $CH_2$; n is 0 or 1; one of $R^3$ and $R^4$ is a pyridinium group which may be substituted and the other is a hydrogen atom or hydrocarbon group which may be substituted, or $R^3$ and $R^4$ taken together may form a quaternalized nitrogen-containing heterocyclic ring which may be substituted, or its ester or its salt, which has a superior anti-bacterial activity, stability, absorbability, etc., a production thereof and a pharmaceutical composition containing it, is provided.

21 Claims, No Drawings

PHOSPHONOCEPHEM DERIVATIVES, PROCESS FOR THE PREPARATION OF THE SAME, AND USE THEREOF

This application is the National Stage of International Application No. PCT/JP98/05709, filed on Dec. 17, 1998.

TECHNICAL FIELD

This invention relates to a novel cephem compound having excellent antibacterial activities on a broad range of Gram-positive and Gram-negative bacteria, especially *Staphylococus aureus*, methicillin-resistant *Staphylococcus aureus* (MRSA) and a bacteria belonging to Pseudomonas and being sufficiently water-soluble, to a method of producing the compound and to a medicine, especially an antibacterial composition containing the compound.

BACKGROUND ART

Various cephem compounds having, at the 7-position, 2-(5-amino-1,2,4-thiadiazole -3-yl)-2(Z)-alkoxy-iminoacetamido group, and having, at the 3-position, 3- or 4-(pyridinium) thiazole-4-ylthio group or condensed heterocyclic ring-thio group containing $N^+$ as a ring constituting atom, have been reported in JPA H9(1997)-100283. However these compounds are not sufficiently soluble in water, and it is preferable to use solubilizing, agents when these compounds are dissolved in water. Thus these compounds are sufficiently satisfactory when they are used in a pharmaceutical preparation, especially for injection.

And various cephem compounds having, at the 7-position, 2-(5-phosphonoamino-1,2,4thiadiazole-3-yl)-2(Z)-methoxyiminoacetamido group, and having at the 3-position, a substituted methyl, i.e., pyridiniummethyl group or 1-methylpyridiniumthiomethyl group which are different from substituted —(CH=CH)$_n$—S-group in chemical structure, have also been reported in JPA S59 (1984)-31791.

Though some recently developed cephalosporin compounds have sufficient activity against methicillin-resistant staphylococcus aureus (MRSA), they are poorly soluble in water or physiologically acceptable saline, which is necessary for administration, and have not been put into practical use. Thus creation of novel compounds, overcoming these problems has been desired.

DISCLOSURE OF INVENTION

Taking the foregoing circumstances into consideration, the present inventors diligently conducted extensive studies and synthesized, for the first time, a cephem compound characterized by having, at the 3-position of its cephem, oxacephem or carbacephem nucleus, a group of the formula:

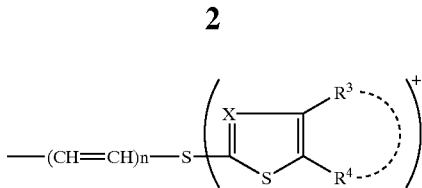

wherein one of $R^3$ and $R^4$ is a pyridinium group which may be substituted and the other is a hydrogen atom or hydrocarbon group which may be substituted, or $R^3$ and $R^4$ taken together may form a quaternalized nitrogen-containing heterocyclic ring which may be substituted; X is a nitrogen atom or CH; and n is 0 or 1, and, at the 7-position, a group of the formula:

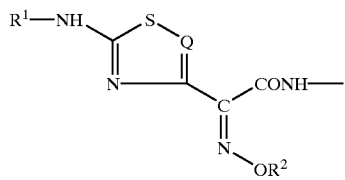

wherein $R^1$ is a phosphono group or a group convertible to a phosphono group; $R^2$ is a hydrogen atom or a group having a linkage through a carbon atom; Q is a nitrogen atom or CH, or an ester or salt thereof, and further found that the compound thus synthesized showed good solubility to water and has excellent medicinal properties such as antibacterial activity.

Based on these findings, the present invention was accomplished.

More specifically, the present invention relates to.

(1) A compound of the formula:

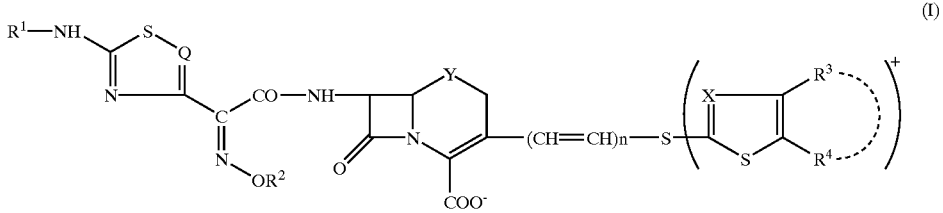

(I)

wherein $R^1$ is a phosphono group or a group convertible to a phosphono group; $R^2$ is a hydrogen atom or a group having a linkage through a carbon atom; each of Q and X is a nitrogen atom or CH; Y is S, O or $CH_2$; n is 0 or 1; one of $R^3$ and $R^4$ is a pyridinium group which may be substituted and the other is a hydrogen atom or hydrocarbon group which may be substituted, or $R^3$ and $R^4$ taken together may form a quaternalized nitrogen-containing heterocyclic ring which may be substituted, salt or ester thereof;

(2) A compound according to the above (1), wherein $R^1$ is a phosphono group which may be protected;

(3) A compound according to the above (1), wherein $R^1$ is phosphono, dialkoxy-phosphoryl, O-alkyl-phosphono, diaminophosphoryl, (amino)(hydroxy)phosphoryl, (alkoxy)(morpholino)phosphoryl or dihalophosphoryl;

(4) A compound according to the above (1), wherein $R^1$ is a phosphono group;
(5) A compound according to the above (1), wherein y is S;
(6) A compound according to the above (1), wherein $R^2$ is a $C_{1-6}$alkyl group which may be substituted or a $C_{3-5}$cycloalkyl group;
(7) A compound according to the above (1), wherein $R^3$ is a pyridinium group which may be substituted and $R^4$ is a hydrogen atom;
(8) A compound according to the above (1), wherein

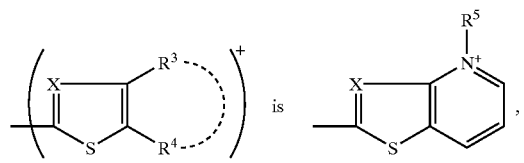
is
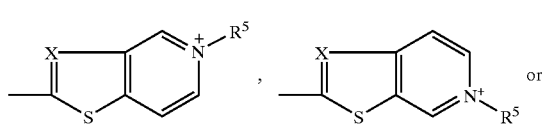,

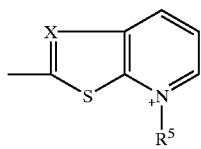

wherein $R^5$ is a hydrocarbon group which may be substituted;
(9) A compound according to the above (1) wherein Q is a nitrogen atom;
(10) A compound according to the above (1), wherein X is a nitrogen atom;
(11) A compound according to the above (1), wherein n is 0;
(12) A compound according to the above (1), which is 7β-[2(Z)-ethoxyimino-2-(5-phosphonoamino-1,2,4-thiadiazole-3-yl)acetamido]-3-[4-(1-methyl-4-pyridinio)-2-thiazolylthio]-3-cephem-4-carboxylate, its ester or its salt;
(13) A compound according to the above (1), which is 7β-[2(Z)-fluoromethoxyimino-2-(5-phosphonoamino-1,2,4-thiadiazole-3-yl)acetamido]-3-[4-(1-methyl-4-pyridinio)-2-thiazolylthio]-3-cephem-4carboxylate, its ester or its salt;

(14) A method for producing a compound shown in the above (1) which comprises reacting a compound of the formula:

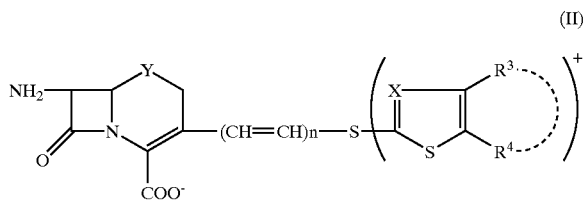

wherein each symbol has the meaning given above, its ester or its salt, with a compound of th e formula:

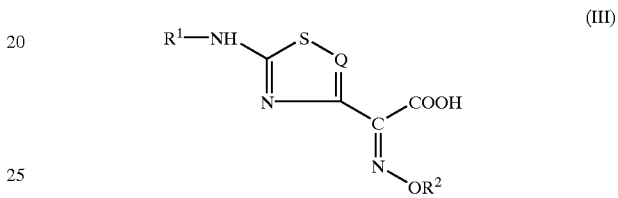

wherein each symbol has the meaning given above, its salt or its reactive derivative, if necessary, followed by converting $R^1$ to a phosphono group;
(15) A method for producing a compound shown in the above (1) which comprises subjecting a compound of the formula:

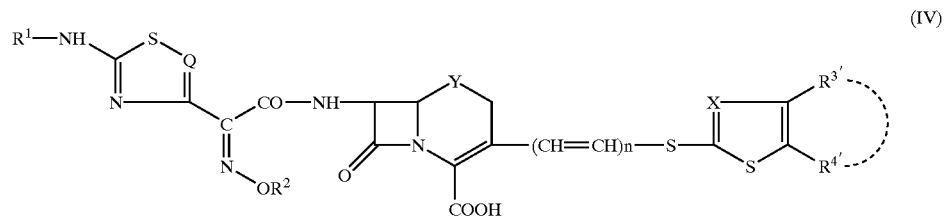

wherein one of $R^{3'}$ and $R^{4'}$ is a pyridyl group which may be substituted, and the other is a hydrogen atom or a hydrocarbon group which may be substituted, or $R^{3'}$ and $R^{4'}$, taken together, represent a nitrogen-containing heterocyclic ring which may be substituted, and the other symbols have the meanings given above, its ester or its salt to the nitrogen quaternalization reaction in which quaternalized-ammonium is formed, if necessary, followed by converting $R^1$ to a phosphono group;
(16) A pharmaceutical composition containing the compound as shown in the above (1);
(17) A pharmaceutical composition containing the compound shown in the above (1) and at least one of pharmaceutically acceptable carriers, diluents and bulking agents;

(18) A pharmaceutical composition as shown in the above (16) which is an anti-bacterial composition;
(19) A pharmaceutical composition as shown in the above (16) which is an anti-MRSA agent;
(20) A pharmaceutical composition as shown in the above (16) which is an injectable composition;
(21) Use of the compound as shown in the above (1) for producing a pharmaceutical composition;
(22) Use as shown in the above (21), wherein the pharmaceutical composition is an antibacterial agent;
(23) Use as shown in the above (21), wherein the pharmaceutical composition is an anti-MRSA agent;
(24) Use as shown in the above (21), wherein the pharmaceutical composition is an injectable composition;
(25) A method for treating a bacterial infection which comprises administering an effective amount of a compound as shown in the above (1) to a patient suffering from the bacterial infection;
(26) A method for treating a bacterial infection which comprises administering an effective amount of a compound as shown in the above (1) together with at least one of pharmaceutically acceptable carriers, diluents and excipients to a patient suffering from the bacterial infection;
(27) A method as shown in the above (25), wherein the bacterial infection is a MRSA infection; and
(28) A method as shown in the above (25), wherein the compound is administered by injection.

BEST MODE FOR CARRYING OUT THE INVENTION

The cephem compound in the present specification includes a group of compounds named on the basis of "cepham" disclosed in "The Journal of The American Chemical Society" Vol. 84, p.3400 (1962), which means a compound, among the cepham compounds, having a double bond at the 3, 4-positions.

Incidentally, the compounds of this invention include the compound of the formula (I) showing the free form or an ester or salt thereof (a salt of the compound (I) or a salt of the ester of the compound (I)). In the present specification, hereinafter, unless otherwise specified, the compound of the formula (I) shown in the free form or an ester or salt thereof is simply referred to as the compound (I) or the antibacterial compound (I). Accordingly, the compound (I) in the present specification includes, usually, the free form as well as an ester or salt thereof.

$R^1$ is a phosphono group or a group convertible to a phosphono group. The group convertible to a phosphono group is a group which can be converted to a phosphono group, for example, by hydrolysis, substitution reaction, etc. Examples of the group convertible to phosphono group include, for example, dihalophosphoryl such as di-chlorophosphoryl, etc. in addition to a protected-phosphono group.

The protected-phosphono group is a phosphono group protected by a phosphono-protective group. In the field of nucleic acid, phosphono-protective groups have been sufficiently studied, and the method of a protecting phosphono group has been established. In the present invention also, conventional phosphono-protective groups can be adequately employed. Examples of protected-phosphono groups include mono-or di-ester phosphono group (e.g., dihalophosphryl such as di-chlorophosphoryl, etc.; dialkoxy-phosphoryl group such as di-methoxyphosphoryl, di-ethoxyphosphoryl, di-propoxyphosphoryl, etc.; O-alkyl-phosphono group such as O-methyl phosphono, O-ethyl phosphono, etc.), mono-esterified mono-amidated phosphono group (e.g., mono-or di-amidated phosphono group such as diaminophosphoryl, (amino)(hydroxy)phosphoryl, etc.; (alkoxy)(amino)phosphoryl group such as (methoxy)(amino)phosphoryl, (ethoxy)(amino)phosphoryl, etc.; (alkoxy)(morpholino)phosphoryl group such as (methoxy)(morpholino)phosphoryl, (ethoxy)(morpholino) phosphoryl, etc.), etc. As $R^1$, phosphono, dialkoxy-phosphoryl, O-alkyl-phosphono, diaminophosphoryl, (amino)(hydroxy)phosphoryl, (alkoxy)(morpholino) phosphoryl or dihalophosphoryl are preferable, and phosphono is the most preferable.

$R^2$ is a hydrogen atom or a group having a linkage through a carbon atom. Examples of the group having a linkage through a carbon atom represented by $R^2$ include, for example, a hydrocarbon group which may be substituted (for example, an alkyl group which may be substituted, an alkenyl group which may be substituted, an alkynyl group which may be substituted, an aralkyl group which may be substituted, a cyclic hydrocarbon group which may be substituted), an acyl group or a non-aromatic heterocyclic group (having linkage at a carbon atom) which may be substituted. Among them, an alkyl group which may be substituted, an alkenyl group which may be substituted, a cyclic hydrocarbon group which may be substituted etc. are preferable. As the alkyl group in "an alkyl group which may be substituted", a $C_{1-6}$alkyl group, etc., are preferable, and methyl, ethyl, isopropyl, etc. are the most preferable. As the alkenyl group in "an alkenyl group which may be substituted", a $C_{2-6}$alkenyl group is preferable. As the alkynyl group in "an alkynyl group which may be substituted", a $C_{2-6}$alkynyl group is preferable. As the aralkyl group in "an aralkyl group which may be substituted", a $C_{7-20}$aralkyl group is preferable. Examples of the cyclic hydrocarbon group in "a cyclic hydrocarbon group which may be substituted" include, a 3 to 7 membered non-aromatic cyclic hydrocarbon group such as cyclopropyl, cyclobutyl, cyclopentyl, cyclohexyl, cycloheptyl, 2-cyclopentene-1-yl, 3-cyclopentene-1-yl, 2-cyclohexene-1-yl, 3-cyclohexene-1-yl, etc., etc. Among them, a $C_{3-7}$cycloalkyl group such as cyclobutyl, cyclopentyl, etc. are preferable. Examples of the acyl group include, for example, a $C_{1-6}$alkanoyl group which may be substituted, a $C_{3-5}$alkenoyl group which may be substituted, a $C_{6-10}$aryl-carbonyl group which may be substituted, a heterocyclic carbonyl group, etc.

As the "optionally substituted $C_{1-6}$alkanoyl group", use is made of, for example, a $C_{1-6}$alkanoyl group which may optionally be substituted with 1 to 3 substituents selected from a halogen, oxo, a $C_{1-6}$alkoxy, a $C_{1-6}$alkanoyl, a $C_{6-10}$aryl, a $C_{6-10}$aryloxy, and a $C_{6-10}$arylthio. More specifically, use is made of, for example, formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, acetoacetyl, 3-oxobutyryl, 4-chloro-3-oxobutyryl, phenylacetyl, p-chlorophenylacetyl, phenoxyacetyl and p-chlorophenoxyacetyl.

As the "optionally substituted $C_{3-5}$alkenoyl group", use is made of, for example, a $C_{3-5}$alkenoyl group optionally substituted with 1 to 3 substituents selected from a halogen and a $C_{6-10}$aryl, more specifically, for example, acryloyl, crotonoyl, maleoyl, cinnamoyl, p-chlorocinnamoyl and β-phenylcinnamoyl.

As the "optionally substituted $C_{6-10}$aryl-carbonyl group", use is made of, for example, al $C_{6-10}$aryl-carbonyl group optionally substituted with 1 to 3 substituents selected from a halogen, nitro, hydroxy, a $C_{1-6}$alkyl and a $C_{1-6}$alkoxy, more specifically, for example, benzoyl, naphthoyl, phthaloyl, p-toluoyl, p-tert-butylbenzoyl, p-hydroxybenzoyl, p-methoxybenzoyl, p-tert-butoxybenzoyl, p-chlorobenzoyl and p-nitrobenzoyl.

The "heterocyclic group" in "heterocyclic carbonyl group" means a group formed by removing one hydrogen atom linked to carbon atom of the heterocyclic ring. The heterocyclic ring means a 5- to 8-membered ring containing 1 to several, preferably 1 to 4 hetero-atoms such as a nitrogen atom which may be oxidized, oxygen atom and a sulfur atom, or a condensed ring thereof. As such a heterocyclic group, for example, 2- or 3-pyrrolyl; 3-, 4- or 5-pyrazolyl; 2-, 4- or 5-imidazolyl; 1,2,3- or 1,2,4-triazolyl; 1H- or 2H-tetrazolyl; 2- or 3-furyl; 2- or 3-thienyl; 2-, 4- or 5-oxazolyl; 3, 4- or 5-isoxazolyl; 1,2,3-oxadiazol-4-yl or 1,2,3-oxadiazol-5-yl; 1,2,4-oxadiazol-3-yl or 1,2,4-oxadiazol-5-yl; 1,2,5- or 1,3,4-oxadiazolyl; 2-, 4- or 5-thiazolyl; 3-, 4- or 5-isothiazolyl; 1,2,3-thiadiazol-4-yl or 1,2,3-thiadiazol-5-yl; 1,2,4-thiadiazol-3-yl or 1,2,4-thiadiazol-5-yl; 1,2,5- or 1,3,4-thiadiazolyl; 2- or 3-pyrrolidinyl; 2-, 3- or 4-pyridyl; 2-, 3- or 4-pyridyl-N-oxido; 3- or 4-pyridazinyl; 3- or 4-pyridazinyl-N-oxido; 2-, 4- or 5-pyrimidinyl; 2-, 4- or 5-pyrimidinyl-N-oxido; pyrazinyl; 2-, 3- or 4-piperidinyl; piperazinyl; 3H-indol-2-yl or 3H-indol-3-yl; 2-, 3- or 4-pyranyl; 2-, 3- or 4thiopyranyl; benzopyranyl; quinolyl; pyrido[2,3-d]pyrimidyl; 1,5-, 1,6-, 1,7-, 1,8-, 2,6- or 2,7-naphthyridyl; thieno[2,3-d]pyridyl; pyrimidopyridyl; pyrazinoquinolyl; and benzopyranyl can be used.

Examples of the non-aromatic heterocyclic group in "non-aromatic heterocyclic group having a linkage at a carbon atom, which may be substituted" preferably include a 3 to 6 membered non-aromatic heterocyclic group containing 1 or 2 hetero atoms such as a nitrogen atom, an oxygen atom, a sulfur atom in addition to a carbon atom, such as oxylanyl, azetidinyl, oxetanyl, thietanyl, pyrrolidinyl, tetrahydrofuryl, thiolanyl, piperidyl, tetrahydropyranyl, morpholinyl, thiomorpholinyl.

Examples of the substituents, which the above-mentioned "hydrocarbon group" may optionally have, include a heterocyclic group, a hydroxyl group, a $C_{1-6}$alkoxy group, a $C_{3-10}$cycloalkyl group, a $C_{3-7}$cycloalkyloxy group, a $C_{6-10}$aryloxy group, a $C_{7-19}$aralkyloxy group, a heterocyclic-oxy group, a mercapto group, a $C_{1-6}$alkylthio group, a $C_{3-10}$cycloalkylthio group, a $C_{6-10}$arylthio group, a $C_{7-19}$aralkylthio group, a heterocyclic-thio group, an amino group, a mono-$C_{1-6}$alkylamino group, a di-$C_{1-6}$alkylamino group, a tri-$C_{1-6}$alkyl ammonium group, a $C_{3-10}$cycloalkylamino group, a $C_{6-10}$arylamino group, a $C_{7-19}$aralkylamino group, a heterocyclic amino group, a cyclic amino group, an azido group, a nitro group, a halogen atom, a cyano group, a carboxyl group, a $C_{1-10}$alkoxy-carbonyl group, a $C_{1-10}$aryloxy-carbonyl group, a $C_{7-19}$aralkyloxy-carbonyl group, a $C_{6-10}$aryl-carbonyl group, a $C_{1-6}$alkanoyl group, a $C_{3-5}$alkenoyl group, a $C_{6-10}$aryl-carbonyloxy group, a $C_{2-6}$alkanoyloxy group, a $C_{3-5}$alkenoyloxy group, an optionally substituted carbamoyl group, an optionally substituted thiocarbamoyl group, an optionally substituted carbamoyloxy group, a phthalimido group, a $C_{1-6}$alkanoylamino group, a $C_{6-10}$arylcarbonylamino group, a $C_{1-10}$alkoxy-carboxamido group, a $C_{6-10}$aryloxy-carboxamido group and a $C_{7-19}$aralkyloxy-carboxamido group. The number of these substituents, which may be the same as or different from one another, ranges from 1 to 4.

Among specific examples of the above-mentioned substituents of the "hydrocarbon group", as the "optionally substituted carbamoyl group", use is made of, for example, a carbamoyl group and a cyclic aminocarbonyl group optionally substituted with one or two substituents selected from, for example, a $C_{1-6}$alkyl group, a $C_{6-10}$aryl group, a $C_{1-6}$alkanoyl group, a $C_{6-10}$arylcarbonyl group and a $C_{1-6}$alkoxy-phenyl group. More specifically, use is made of, for example, carbamoyl, N-methylcarbamoyl, N-ethylcarbamoyl, N,N-dimethylcarbamoyl, N,N-diethylcarbamoyl, N-phenylcarbamoyl, N-acetylchrbamoyl, N-benzoylcarbamoyl, N-(p-methoxyphenyl)carbamoyl, pyrrolidinocarbonyl, piperidinocarbonyl, piperazinocarbonyl and morpholinocarbonyl. As the "optionally substituted thiocarbamoyl group", use is made of a thiocarbamoyl group optionally substituted with one or two substituents selected from[ f]or example, a $C_{1-6}$alkyl group and a $C_{6-10}$aryl group, which are exemplified by thiocarbamoyl, N-methylthiocarbamoyl and N-phenylthiocarbamoyl. As the "optionally substituted calrbamoyloxy group", use is made of a carbamoyloxy group optionally substituted with one or two substituents selected from[ f]or example, a $C_{1-6}$alkyl group and a $C_{6-10}$aryl group. Specific examples include carbamoyloxy, N-methyl carbamoyloxy, N,N-d(methyl carbamoyloxy, N-ethyl carbamoyloxy and N-phenyl carbamoyloxy.

As the heterocyclic group and the heterocyclic group in the heterocyclic-oxy group, the heterocyclic-thio group and the heterocyclic amino group in the substituent of the "hydrocarbon group", use is made of group;similar to those in the "heterocyclic carbonyl group" as mentioned above.

Examples of the substituent in the "non-aromatic heterocyclic group having a linkage at a carbon atom, which may be substituted" mentioned above include the embodiments mentioned as the hydrocarbon group and its substituent in the "hydrocarbon group which may be substituted".

As $R^2$, an optionally substituted hydrocarbon group is preferable. Examples of the "optionally substituted hydrocarbon group" shown by $R^3$ include a $C_{1-6}$alkyl group optionally substituted with one to three substituents selected from, for example, a hydroxyl group, a $C_{3-10}$cycloalkyl group, a $C_{1-6}$alkoxy group, a $C_{1-6}$alkylthio group, an amino group, a halogen atom, carboxyl group, a $C_{1-10}$alkoxycarbonyl group, an optionally substituted carbamoyl group, a cyano group, an azido group and a heterocyclic group, which are more specifically exemplified by cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, fluoromethyl, 2-fluoroethyl, 2,2-difluoroethyl, chloromethyl, 2-chloroethyl, 2,2-dichloroethyl, 2,2,2-trichloroethyl, 2-bromoethyl, 2-iodoethyl, 2,2,2-trifluoroethyl, carboxymethyl, 1-carboxyethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, N-methylcarbamoylmethyl, N,N-dimethylcarbamoylmethyl, 2-azidoethyl, 2-(pyrazolyl)ethyl, 2-(imidazolyl)ethyl, 2-(2-oxopyrrolidin-3-yl)ethyl and 1-carboxyl-1-(2,3,4-trihydroxyphenyl)methyl. Most preferable examples of $R^2$ include, for example, a straight chain or branched $C_{1-6}$alkyl group which may be substituted with one to three substituents selected from a halogen, a hydroxyl a $C_{1-6}$alkoxy group, a carboxyl group, a $C_{1-10}$alkoxy-carbonyl group, a cyano group, a carbamoyl group and a substituted carbamoyl, such as methyl, ethyl, n-propyl, isopropyl, butyl, isobutyl, sec-butyl, fluoromethyl, 2-fluoroethyl, 2-chloroethyl, 2-hydroxyethyl, 2-methoxyethyl, cyanomethyl, carboxymethyl, methoxycarbonylmethyl, ethoxycarbonylmethyl, carbamoylmethyl, N-methylcarbamoylmethyl, N,N-dimethylcarbamoylmethyl, etc., a $C_{3-5}$cycloalkyl group such as cyclopropyl, cyclobutyl, cyclopentyl, etc. and a $C_{3-5}$cycloalkyl-$C_{1-3}$alkyl group such as cyclopropylmethyl, etc. Among them, a $C_{1-6}$alkyl group which may be substituted and $C_{3-5}$cycloalkyl group are preferable.

One of $R^3$ and $R^4$ is a pyridinium group which may be substituted and the other is a hydrogen atom or a hydrocarbon group which may be substituted, or $R^3$ and $R^4$, taken together, represent a heterocyclic group which may be substituted containing a quaternalized nitrogen. Examples of the "pyridinium group which may be substituted" include, for example, a group of the formula:

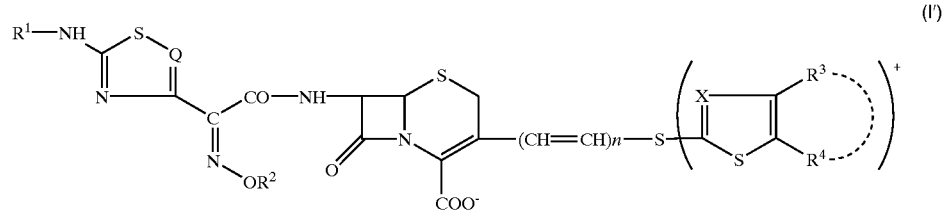

(I')

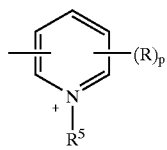

wherein $R^5$ is a hydrocarbon group which may be substituted, R is a $C_{1-6}$alkyl group, a $C_{1-6}$alkoxy group, a $C_{1-6}$alkoxy-carbonyl group, a amino group, a nitro group, a halogen atom or a carboxy group, p is an integer of from 0 to 4, etc.

In case that $R^3$ and $R^4$, taken together, represent a heterocyclic group containing a quaternalized nitrogen, which may be substituted, the group of the formula:

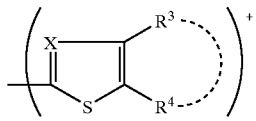

includes 6 membered unsaturated heterocyclic groups such as

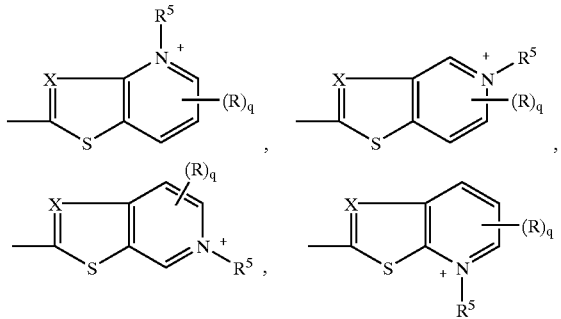

wherein q is an integer of 0 to 3, and the other symbols have the meanings given above, etc.

Examples of the "hydrocarbon group which may be substituted" represented by $R^3$, $R^4$ or $R^5$ include those mentioned in the explanation of "a group having a linkage through a carbon atom" represented by $R^2$.

Each of p and q is preferably 0.

$R^5$ is preferably is a $C_{1-4}$alkyl group such as methyl, etc. Referring to $R^3$ and $R^4$, it is preferable that $R^3$ is a pyridinium group which may be substituted and $R^4$ is a hydrogen atom, or that $R^3$ and $R^4$, taken to represent a 6 membered unsaturated heterocyclic group having a quaternalized nitrogen atom.

Each of Q and X is a nitrogen atom or CH. Each of Q and X is preferably a nitrogen atom.

Y is S, O or $CH_2$. Y is preferably S. That is, among the compound (I), a compound of the formula:

wherein each symbol has the meaning given above, its ester or its salt is preferable. While n can be 0 or 1, it is preferably 0.

In the above-mentioned compound (I), the mark [—] attached on the right shoulder of —COO at the 4-position shows that the carboxyl group forms carboxylate anion, making a pair with the positive charge on the pyridine ring (hereinafter sometimes simply referred to as $A^+$). On the other hand, the compound (I) may optionally form a pharmaceutically acceptable ester or salt. As the pharmaceutically acceptable salt, use is made of, for example, inorganic basic salts, ammonium salts, organic basic salts, inorganic acid addition salts, organic acid addition salts and basic amino acid salts. As the inorganic base capable of forming the inorganic basic salt, use is made of, for example, alkali metal (e.g. sodium and potassium) and alkaline earth metals (e.g. calcium); as the organic base capable of forming the organic basic salt, use is made of, for example, procaine, 2-phenylethyl benzylamine, dibenzylethylenediamine, ethanolamine, diethanolamine, trishydroxymethylaminomethane, polyhydroxyalkylamine and N-methylglucosamine; as an inorganic acid capable of forming the inorganic acid addition salt, use is made of, for example, hydrochloric acid, hydrobromic acid, sulfuric acid, nitric acid and phosphoric acid; as an organic acid capable of forming the organic acid addition salt, use is made of, for example, p-toluenesulfonic acid, methanesulfonic acid, formic acid, trifluoroacetic acid and maleic acid; and, as a basic amino acid capable of forming the basic amino acid salt, use is made of, for example, lysine, arginine, ornithine and histidine. Among these salts, a basic salt (i.e. an inorganic basic salt, an ammonium salt, an organic basic salt and a basic amino acid salt) means that capable of being formed in the case where a basic group such as amino group, a monoalkylamino group, a dialkylamino group, a cycloalkylamino group, an arylamino group, an aralkylamino group, a cyclic amino group and a N-containing heterocyclic group exists in the substituent $R^1$, $R^2$ or $R^5$ of the compound (I). And, examples of the acid addition salt include a salt in which the substituent at 4-position is a carboxyl group (COOH) and the substituent at 3-position is —(CH=CH)$_n$—S—$A^+Z^-$ [wherein $Z^-$ stands for anion formed by removing proton $H^+$ from the inorganic acid or the organic acid, the anion being exemplified by a chloride ion, a bromide ion, a sulfate ion, a p-toluenesulfonate ion, a methanesulfonate ion and a trifluoroacetate ion, etc.] the salt being formed by adding one mole of acid to the moiety forming the internal salt of the compound (I), i.e. the carboxylate moiety (COO$^-$)

at the 4-position and heterocyclic ring moiety at the 3-position. The ester derivative of the compound (I) means an ester producible by esterifying the carboxyl group in the molecule which is utilizable as an intermediate of the synthesis and is metabolically unstable and a non-toxic ester. Examples of the ester utilizable as intermediate of the synthesis include an optionally substituted $C_{1-6}$alkyl ester, a $C_{1-6}$alkyl ester, a $C_{3-10}$cycloalkyl ester, a $C_{3-10}$cycloalkyl-$C_{1-6}$alkyl ester, an optionally substituted $C_{6-10}$aryl ester, an optionally substituted $C_{7-12}$aralkyl ester, a di-$C_{6-10}$aryl-methyl ester, a tri-$C_{6-10}$aryl-methyl ester, a substituted silyl ester and a $C_{2-6}$alkanoyloxy-$C_{1-6}$alkyl ester.

As the "optionally substituted $C_{1-6}$alkyl ester", use is made of, for example, methyl, ethyl, n-propyl, isopropyl, n-butyl, isobutyl, sec-butyl, tert-butyl, n-pentyl and n-hexyl, which may be substituted with one to three of, for example, benzyloxy, a $C_{1-4}$alkyl sulfonyl (e.g. methyl sulfonyl), trimethylsilyl, a halogen (e.g. fluorine, chlorine and bromine), acetyl, nitrobenzoyl, mesylbenzoyl, phthalimido, succinimide, benzenesulfonyl, phenylthio, a di-$C_{1-4}$alkylamino (e.g. dimethylamino), pyridyl, a $C_{1-4}$alkyl sulfinyl (e.g. methyl sulfinyl) and cyano. Examples of such groups include benzyloxymethyl, 2-methylsulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-oxido-2-methyl, methylsulfinylmethyl and 2-cyano-1,1-dimethylethyl.

As the $C_{2-6}$alkenyl group forming the "$C_{2-6}$alkenyl ester", use is made of, for example, vinyl, allyl, 1-propenyl, isopropenyl, 1-butenyl, 2-butenyl, 3-butenyl, methallyl, 1,1-dimethylallyl and 3-methyl-3-butenyl.

As the C3-10cycloalkyl group forming the "$C_{3-10}$cycloalkyl ester", use is made of, for example, cyclopropyl, cyclobutyl, cyclopentyl, cyclohexyl, cycloheptyl, norbornyl and adamantyl.

As the $C_{3-10}$cycloalkyl -$C_{1-6}$alkyl group forming the "$C_{3-10}$cycloalkyl-$C_{1-6}$alkyl ester", use is made of, for example, cyclopropylmethyl, cyclopentylmethyl and cyclohexylmethyl.

As the "$C_{6-10}$aryl group" forming the "optionally substituted $C_{6-10}$aryl ester", use is made of, for example, phenyl, α-naphthyl, β-naphthyl and biphenylyl, which may optionally be substituted with one to three of, for example, nitro and a halogen (e.g. fluorine, chlorine and bromine). The above group is specifically exemplified by p-nitrophenyl and p-chlorophenyl.

As the "$C_{7-12}$aralkyl group" forming the "optionally substituted $C_{7-12}$aralkyl ester", use is made of, for example, benzyl, 1-phenylethyl, 2-phenylethyl, phenylpropyl and naphthylmethyl, which may optionally be substituted with one to three of, for example nitro, a $C_{1-4}$alkoxy (e.g. methoxy), a $C_{1-4}$alkyl (e.g. methyl and ethyl) and hydroxy. Specific examples of such group include p-nitrobenzyl, p-methoxybenzyl and 3,5-di-tert-butyl-4-hydroxybenzyl.

As the di-$C_{6-10}$aryl-methyl group forming the "di-$C_{6-10}$aryl-methyl ester", use is made of, among others, benzhydryl; as the tri-$C_{6-10}$aryl-methyl group forming the tri-$C_{6-10}$aryl-methyl ester, use is made of, among others, trityl; as the substituted silyl group forming the substituted silyl ester, use is made of, for example, trimethylsilyl, tert-butyldimethylsilyl and —Si(CH$_3$)$_2$CH$_2$CH$_2$Si(CH$_3$)$_2$—. As the $C_{2-6}$alkanoyloxy-$C_{1-6}$alkyl ester, use is made of, for example, acetoxymethyl ester. Examples of the above-mentioned ester include an ester at 4-position. The compound, wherein the substituent at 4-position is the above-mentioned ester group, forms a salt in which the substituent at 3-position is —(CH=CH)$_n$—S—A$^+$Z$^-$ [wherein symbols are of the same meaning as defined above].

The present invention includes, besides the above-described ester derivatives, pharmacologically acceptable compounds convertible into the compound (I) in vivo.

The compound (I) and starting compounds of this invention, in case that n is 1, include cis-isomer (Z-compound), trans-isomer (E-compound) and a cis-trans mixture. The compound (I) of this invention is preferably a trans-isomer (E-compound).

Referring to the compound (I), the cis-isomer (Z-compound), for example, means one of the geometrical isomers having the partial structure represented by the formula:

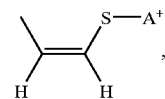

and the trans-isomer means a geometrical isomer having the partial structure of the formula:

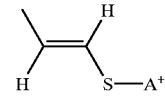

Among the compound (I), for example, 7β-[2(Z)-ethoxyimino-2-(5-phosphonoamino-1,2,4-thiadiazole-3-yl)acetamido]-3-[4-(1-methyl-4-pyridinio)-2-thiazolylthio]-3-cephem-4-carboxylate, its ester, its salt, 7β-[2(Z)-fluoromethoxyimino-2-(5-phosphonoamino-1,2,4-thiadiazole-3-yl)acetamido]-3-[4-(1-methyl-4-pyridinio)-2-thiazolylthio]-3-cephem-4-carboxylate, its ester and its salt, are especially preferable.

In the present specification, specific examples of the respective substituents are, unless specifically described, as follows.

halogen: fluoro, chloro, bromo, iodo, etc.;

$C_{1-4}$alkyl group: methyl, ethyl, propyl, isopropyl, butyl, isobutyl, t-butyl, etc.;

$C_{1-6}$alkyl group: the above mentioned $C_{1-4}$alkyl group and pentyl, 2,2-dimethyl propyl, hexyl, etc.;

$C_{2-6}$alkenyl group: vinyl, allyl, 1-propenyl, isopropenyl, 1-butenyl, 2-butenyl, 3-butenyl, methallyl, 1,1-dimethyl allyl, etc.;

$C_{2-6}$alkynyl group: ethynyl, 1-propynyl, 2-propynyl, 2-butynyl, 2-pentynyl, 2-hexynyl, etc.;

$C_{3-5}$cycloalkyl group: cyclopropyl, cyclobutyl, cyclopentyl, etc.;

$C_{3-10}$cycloalkyl group: the above mentioned $C_{3-5}$cycloalkyl group and cyclohexyl, cycloheptyl, cyclooctyl, cyclodecyl, etc.;

$C_{6-10}$aryl group: phenyl, naphthyl, etc.;

$C_{7-20}$aralkyl group: benzyl, 1-phenyl ethyl, 2-phenyl ethyl, phenyl propyl, naphthyl methyl, benzhydryl, etc.;

$C_{1-6}$alkoxy group: methoxy, ethoxy, propoxy, isopropoxy, butoxy, isobutoxy, t-butoxy, pentyloxy, 2,2-dimethyl propyloxy, hexyloxy, etc.;

$C_{3-7}$cycloalkyloxy group: cyclopropyloxy, cyclobutyloxy, cyclopentyloxy, cyclohexyloxy, etc.;

$C_{6-10}$aryloxy group: phenoxy, naphthyloxy, etc.;

$C_{7-19}$aralkyl-oxy group: benzyloxy, 1-phenylethyloxy, 2-phenylethyloxy, benzhydryloxy, etc.;

$C_{1-6}$alkyl-thio group: methylthio, ethylthio, propylthio, butylthio, isobutylthio, t-butylthio, pentylthio, 2,2-dimethylpropylthio, hexylthio, etc.;

$C_{3-10}$cycloalkyl-thio group: cyclopropylthio, cyclobutylthio, cyclopentylthio, cyclohexylthio, cycloheptylthio, cyclooctylthio, cyclodecylthio, etc.;

$C_{6-10}$aryl-thio group: phenylthio, naphthylthio, etc.;

$C_{7-19}$aralkyl-thio group: benzylthio, phenylethylthio, benzhydrylthio, tritylthio, etc.;

$C_{1-4}$alkyl-sulfinyl group methylsulfinyl, ethylsulfinyl, propylsulfinyl, isopropylsulfinyl, butylsulfinyl, t-butylsulfinyl, etc.;

$C_{1-4}$alkyl-sulfonyl group: methylsulfonyl, ethylsulfonyl, propylsulfonyl, isopropylsulfonyl, butylsulfonyl, isobutylsulfonyl, t-butylsulfonyl, etc.;

mono-$C_{1-6}$alkyl-amino group: methylamino, ethylamino, n-propylamino, n-butylamino, etc.;

di-$C_{1-4}$alkyl-amino group dimethylamino, diethylamino, methylethylamino, di-(n-propyl)amino, di-(n-butyl) amino, etc.;

di-$C_{1-6}$alkyl1-amino group: the above mentioned di-$C_{1-4}$alkyl amino group and di-(pentyl)amino, di-(n-hexyl)amino, etc.;

tri-$C_{1-6}$alkyl-ammonium group trimethylammonium, etc.;

$C_{3-10}$cycloalkyl-amino group cyclopropylamino, cyclopentylamino, cyclohexylamino, etc.;

$C_{6-10}$aryl-amino group: anilino, N-methylanilino, etc.;

$C_{7-19}$aralkyl-amino group: benzylamino, 1-phenylethylamino, 2-phenylethyl amino, benzhydrylamino, etc.;

Cyclic amino group: pyrrolidino, piperidino, piperazinyl, morpholino, 1-pyrrolyl, etc.;

$C_{1-6}$alkanoyl amino group: acetamido, propionamido, butyroamido, valeroamido, pivaloamido, etc.;

$C_{6-10}$aryl-carbonyl amino group benzamido, naphthoylamido, phthalimide, etc.;

$C_{1-6}$alkanoyl group: formyl, acetyl, propionyl, butyryl, valeryl, pivaloyl, succinyl, glutaryl, etc.;

$C_{2-6}$alkanoyloxy group: acetoxy, propionyloxy, butyryloxy, valeryloxy, pivaloyloxy, etc.;

$C_{3-5}$alkenoyl group: acryloyl, crotonoyl, maleoyl, etc.;

$C_{3-5}$alkenoyl-oxy group: acryloyloxy, crotonoyloxy, maleoyloxy, etc.;

$C_{6-10}$aryl-carbonyl group benzoyl, naphthoyl, phthaloyl, phenyl acetyl, etc.;

$C_{6-10}$aryl-carbonyloxy group: benzoyloxy, naphthoyloxy, phenylacetoxy, etc., $C_{1-6}$alkoxy-phenyl group: methoxyphenyl, ethoxyphenyl, propoxyphenyl, butoxy phenyl, t-butoxyphenyl, etc.;

$C_{1-10}$alkoxy-carbonyl group: methoxycarbonyl, ethoxycarbonyl, propoxycarbonyl, isopropoxycarbonyl, butoxycarbonyl, isobutoxycarbonyl, t-butoxycarbonyl, pentyloxycarbonyl, 2,2-dimethylpropyloxycarbonyl, hexyloxycarbonyl, heptyloxycarbonyl, decyloxycarbonyl, etc.;

$C_{2-10}$alkenyloxy-carbonyl group allyloxycarbonyl, etc.;

$C_{6-10}$aryloxy-carbonyl group: phenoxycarbonyl, naphthyloxycarbonyl, etc.;

$C_{7-19}$aralkyl-oxycarbonyl group: benzyloxycarbonyl, benzhydryloxycarbonyl, etc.;

$C_{1-10}$alkoxy-carboxamido group methoxycarboxamido ($CH_3OCONH-$), ethoxycarboxamido, tert-butoxycarboxamido, etc.;

$C_{6-10}$aryloxy-carboxamido group: phenoxycarboxamido ($C_6H_5OCONH-$), etc.

Methods of producing the compound (I) of this invention are hereinafter described in detail.

Production Method (1):

The compound (I) can be synthesized by allowing, for example, a compound of the formula (II) or an ester or salt thereof (hereinafter referred to as Compound (II)) to react with a compound of the formula (III) or its salt or a reactive derivative thereof (hereinafter referred to as Compound (III)), followed by removing the protective group so as to change the group $R^1$ to a phosphono group.

The present method is to acylate a compound (II) by using compound (III). Compound (II) can be used as it is, and can also be used as its salt or its ester.

Examples of the salts of Compound (II) include an inorganic basic salt, an ammonium salt, an organic basic salt, an inorganic acid addition salt and an organic acid addition salt. Examples of inorganic basic salts include an alkali metal salt (e.g. sodium salt and potassium salt) and an alkaline earth metal salt (e.g. calcium salt); examples of an organic basic salt include trimethylamine salt, triethylamine salt, tert-butyldimethylamine salt, dibenzylmethylamine salt, benzyldimethylamine salt, N,N-dimethylaniline salt, pyridine salt and quinoline salt; examples of the inorganic acid addition salts include hydrochloride, hydrobromide, sulfate, nitrate and phosphate; and examples of the organic acid addition salts include formate, acetate, trifluoroacetate, methanesulfonate and p-toluenesulfonate.

As the ester of amino compound (II), mention is made of esters already described as the ester derivatives of compound (I), as exemplified by, more specifically, a $C_{1-6}$alkyl ester, a $C_{2-6}$alkenyl ester, a $C_{3-10}$cycloalkyl ester, a $C_{3-6}$cycloalkyl-$C_{1-6}$alkyl ester, a $C_{6-10}$aryl ester, a $C_{7-12}$aralkyl ester, a di-$C_{6-10}$arylmethyl ester, a tri-$C_{6-10}$arylmethyl ester and a $C_{2-6}$alkanoyloxy-$C_{1-6}$alkyl ester.

Compound (II) can be produced by the method shown in, for example, JPA-H9(1997)-100283, etc.

In this method, Compound (III) in the free state or in the form of a salt or reactive derivative thereof can be used as an agent for acylating the amino group at the 7-position of Compound (III). Examples of the salts of Compound (III) includes inorganic basic salts and organic basic salts. Examples of inorganic basic salts include alkali metal salts (e.g. sodium salt and potassium salt) and alkaline earth metal salts (e.g. calcium salt); examples of the organic basic salts include trimethylamine salt, triethylamine salt, tert-butyldimethylamine salt, dibenzylmethylamine salt, benzyldimethylamine salt, N,N-dimethylaniline salt, pyridine salt and quinoline salt.

In this method, the compound (III) as it is, its salt or its reactive derivative is used as an acylating agent for acylation of the amino group at the 7-position of amino compound. Examples of the salt of compound (III) include an inorganic base salt and an organic base salt. Examples of the inorganic base salt include alkali metal salt (e.g. sodium salt, potassium salt, etc.), alkaline earth metal salt (e.g., calcium salt, etc.), etc., and examples of the organic base salt include trimethylamine salt, triethylamine salt, tert-butyl dimethylamine salt, dibenzyl methylamine salt, benzyl dimethylamine salt, N,N-dimethyl aniline salt, pyridine salt, quinoline salt etc. Examples of the reactive derivative of the carboxylic acid (III) include, for example, acid halides, acid azides, acid anhydrides, mixed acid anhydrides, active amides, active esters, active thio esters, etc. Examples of the acid halides include, for example, acid chloride, acid bromide, etc.; examples of the mixed acid anhydrides include mono-$C_{1-6}$alkyl-carbonic acid mixed acid anhydrides (e.g. mixed acid anhydride of free acid and monomethylcarbonic acid, monoethylcarbonic acid, mono-isopropylcarbonic acid, mono-isobutylcarbonic acid, mono-tert-butylcarbonic acid, mono-benzylcarbonic acid, mono-(p-nitrobenzyl)carbonic acid, mono-allylcarbonic acid, etc.), a $C_{1-6}$aliphatic carboxylic acid mixed acid anhydride (e.g. mixed acid anhydride of free acid and acetic acid, trichloroacetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), a $C_{7-12}$ aromatic carboxylic acid mixed acid anhydride (e.g. mixed acid anhydride of free acid and benzoic acid, p-toluic acid, p-chloro benzoic acid, etc.), organic sulfonic acid mixed acid anhydrides (e.g. mixed acid anhydride of free acid and methanesulfonic acid, ethane sulfonic acid, benzenesulfonic acid, p-toluenesulfonic acid, etc.) etc.; examples of the active amide include an amide with a nitrogen-containing heterocyclic compound (acid amide of a free acid and, for example; pyrazole, imidazole, benzo triazole, etc., these nitrogen-containing heterocyclic compound may be substituted with a $C_{1-6}$alkyl group (e.g., methyl, ethyl, etc.), a $C_{1-6}$alkoxy group (e.g., methoxy, ethoxy, etc.), a halogen atom (e.g., fluorine, chlorine, bromine, etc.), an oxo group, a thioxo group, a $C_{1-6}$alkylthio group (e.g., methylthio, ethylthio, etc.), etc.), etc.

As an active ester, all the active esters used in the field of the synthesis of β-lactam and peptide may be used. Examples of the active ester include, for example, an organic phosphoric acid ester (e.g. di-ethoxyphosphoric acid ester, di-phenoxyphosphoric acid ester, etc.), p-nitrophenyl ester, 2,4-di-nitrophenyl ester, cyanomethyl ester, pentachlorophenyl ester, N-hydroxysuccinimide ester, N-hydroxy phthalimide ester, 1-hydroxy benzotriazole ester, 6-chloro-1-hydroxybenzotriazole ester, 1-hydroxy-1H-2-pyridone ester, etc. Examples of the active thio ester include an ester of the acid with an aromatic heterocyclic thiol compound (e.g. 2-pyridylthiol ester, 2-benzothiazolylthiol ester, etc., which heterocyclics may be substituted with a $C_{1-6}$alkyl group (e.g. methyl, ethyl, etc.), a $C_{1-6}$alkoxy group (e.g., methoxy, ethoxy, etc.), a halogen atom (e.g., fluorine, chlorine, bromine, etc.), a $C_{1-6}$alkyl-thio group (e.g., methylthio, ethylthio, etc.), etc.).

The Compound (III) may easily be produced by a known method (e.g. a method shown in JPA S60(1985)-231684, JPA S62(1987)-149682, EP0590681, etc.) or a method similar to the known method. The reaction derivative of Compound (III) can be reacted with Compound (II) after isolation from the reaction mixture, and the reaction mixture containing the reactive derivative of Compound (III) can also be used for the reaction with Compound (II). When Compound (III) is used in the form of a free acid or a salt, a pertinent condensing agent is used. Excamples of the condensing agent include, for example, a N,N'-di-substituted carbodiimide such as N,N'-di-cyclohexylcarbodiimide, etc., an azolide reagent such as N,N'-carbonyldiimidazole, N,N'-thiocarbonyldiimidazole, etc., a dehydrating agent such as N-ethoxycarbonyl-2-ethoxy-1,2-dihydroquinoline, phosphorus oxychloride, an alkoxy-acetylene, etc., a 2-halogeno pyridinium salt such as 2-chloropyridiniummethyl iodide, 2-fluoropyridiniummethyl iodide, etc. When these condensing agents are used, the reaction proceeds through a reactive derivative of Compound (III). The reaction is usually carried out in a solvent which does not interfere with the reaction. Examples of the solvent include, for example, an ether such as dioxane, tetrahydrofuran, diethyl ether, tert-butyl methyl ether, diisoprpyl ether, ethylene glycol-dimethyl ether, etc , an ester such as ethyl formate, ethyl acetate, acetic acid n-butyl, etc., a halogenated hydrocarbon such as dichloromethane, chloroform, carbon tetrachloride, trichlene, 1,2-dicholoroethane, etc., a hydrocarbon such as n-hexane, benzene, toluene, etc., an amide such as formamide, N,N-dimethylformamide, N,N-dimethylacetamido, etc., a ketone such as acetone, methylethylketone, methylisobutylketone, etc., a nitrile such as acetonitrile, propionitrile, etc., dimethylsulfoxide, sulfolane, hexamethylphosphoramide, water, etc. These solvents may be used alone or in combination of two or more.

The amount of Compound (III) used is usually 1 to 5 moles, preferably about 1 to 2 moles per mole of Compound (II). The reaction is usually conducted in a temperature of from about −80 to 80° C., preferably from about −40 to 50° C., more preferably from about −30 to 30° C. The reaction time varies depending upon the kind of Compound (II) and Compound (III), the kind of solvent used (ratio of a solvent in case of using a mixed solvent) and the reaction temperature, and is usually about 1 minute to 72 hours, preferably about 15 minutes to 3 hours. When an acid halide is used as the acylating agent, the reaction may be carried out in the presence of a acid scavenger in order to eliminate from the reaction system a hydrogen halide formed by the reaction.

Examples of the acid scavenger include, for example, an inorganic base such as sodium carbonate, potassium carbonate, calcium carbonate, sodium hydrogen carbonate, etc., a tertiary amine such as triethylamine, tri-(n-propyl) amine, tri-(n-butyl)amine, diisopropylethylamine, cyclohexyldimethylamine, pyridine, lutidine, γ-collidine, N,N-dimethylaniline, N-methyl piperidine, N-methylpyrrolidine, N-methylmorpholine, etc., an alkylene oxide such as propylene oxide, epichlorohydrin etc., etc. In case that $R^1$ is a hydrogen atom and a phosphono group is introduced when the reaction derivative forms, the reaction mixture containing reaction product wherein $R^1$ is a dihalophosphoryl group, may be deprotected by treating with water to obtain a compound (I) wherein $R^1$ is a phosphono group, or may be treated with an an alkanol such as methanol, ethanol, etc., to obtain a compound (I) wherein $R^1$ is an esterified phosphono group.

Production Method (2):

Among Compound (I), a compound of the formula:

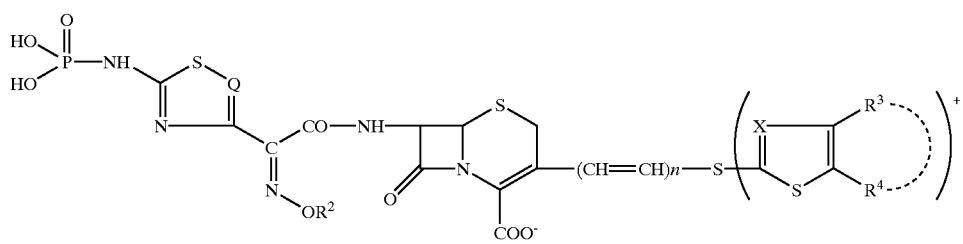

(Ia)

wherein each symbol has the meaning given above, or salt thereof (hereinafter sometimes referred to as Compound (Ia)) can be produced by subjecting a compound of the formula:

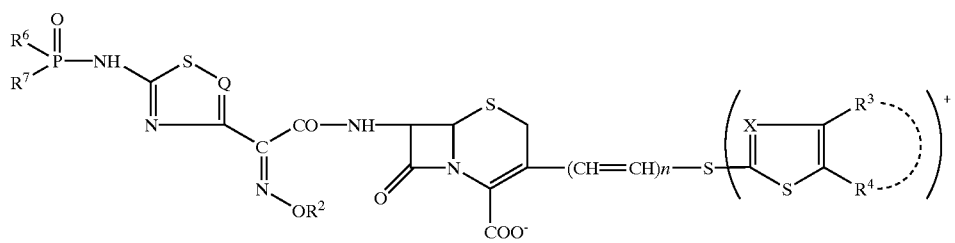

(Ib)

wherein $R^6$ and $R^7$ represent, the same or different, a protecting group of phosphono group, the other symbols have the meanings given above, or a salt thereof (hereinafter sometimes referred to as Compound (Ib)) to the deprotection reaction so that the protected phosphono group is deprotected.

Examples of the protecting group of a phosphono group represented by $R^6$ or $R^7$ include, for example, a halogen (e.g. chlorine atom, etc.), an alkoxy (e.g., a $C_{1-3}$alkoxy group such as methoxy, ethoxy, propoxy, etc.), amino, morpholino, thiomorpholino, etc.

The present method can be carried out, for example, by reacting Compound (Ib) with a halogenated trimethylsilyl such as trimethylsilyl bromide, trimethylsilyl iodide, trimethylsilyl chloride, etc., a metal halide such as sodium iodide, potassium iodide, sodium bromide, etc., an alkali metal thiocyanate such as sodium thiocyanate, potassium thiocyanate, etc., etc. The reaction is carried out in a solvent which does not interfere with the reaction, though examples of the preferable solvent include methylene chloride, dimethylacetamide, etc. The reaction temperature is not limiting and the reaction is carried out usually under cooling or under mild conditions like slight heating.

When $R^6$ and $R^7$ in Compound (Ib) are different, a protecting group of only one of $R^6$ and $R^7$ in Compound (Ib) can be removed by selecting the reaction condition. In this case, compound of the formula:

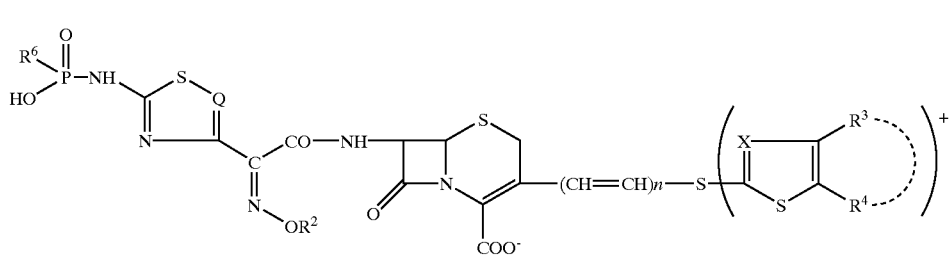

(Ic)

wherein each symbol has the meaning given above, or salt thereof (hereinafter sometimes referred to as Compound (Ic)) is obtained.

Production Method (3):

Compound (Ia) can be produced, for example, by subjecting Compound (Ic) to a deprotecting reaction for removing the protecting group of the phosphono group.

The present method can be carried out, for example, by treating Compound (Ic) with an acid. The acid may be an organic acid or an inorganic acid. Preferable examples of the acid include, for example, formic acid, sulfuric acid, trifluoroacetic acid, benzenesulfonic acid, nitric acid, p-toluenesulfonic acid, hydrochloric acid, etc. More preferable examples of the acid include, for example, formic acid, trifluoroacetic acid, hydrochloric acid, etc. The acid suitable for the reaction is selected by taking the group which is hydrolyzed into consideration. The reaction can be carried out with or without a solvent. Examples of the suitable solvent include an organic solvent, water, mixed solvent thereof, etc., which is usually used as a solvent. When trifluoroacetic acid is used, the reaction is preferably carried out in the presence of anisole.

Production Method (4)

Compound (I) can be produced by condensing a compound of the formula:

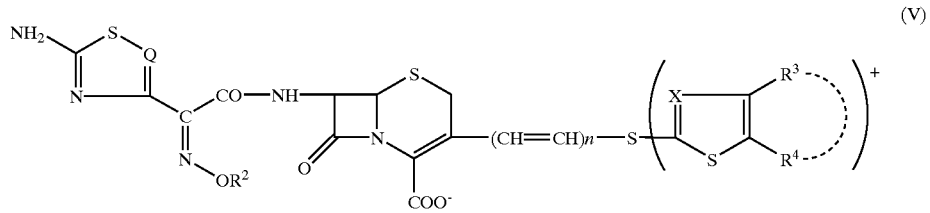

(V)

wherein each symbol has the meaning given above, or a salt thereof (hereinafter sometimes referred to as Compound (V)) and a phosphoric acid derivative.

The reaction can be carried out by using Compound (V) or a salt thereof and a phosphorus halide such as phosphorus trichloride, phosphorus pentachloride, etc., etc. The reaction is usually carried out in a solvent such as a halogenated alkylene (e.g. methylene chloride, ethylene chloride, etc.), toluene, etc. The reaction temperature is not limiting and the reaction is carried out usually under cooling, an ambient temperature or under mild conditions like slight heating. In this reaction, when the reaction mixture contains:Compound (I) wherein $R^1$ is dihalophosphoryl group, the reaction mixture may further be treated either with water to give Compound (I) wherein $R^1$ is phosphono group or with an alcohol (alkanol such as methanol, ethanol, etc.) to give Compound (I) wherein $R^1$ is an esterified phosphono group.

Compound (I) produced by the above production methods (1) to (4) can be isolated and purified by known methods, for example, extraction, column chromatography, precipitation, recrystallization, etc. On the other hand, isolated Compound (I) can be converted to a physiologically acceptable salt by a known method.

The method for producing the starting compound (III) is explained as follows:

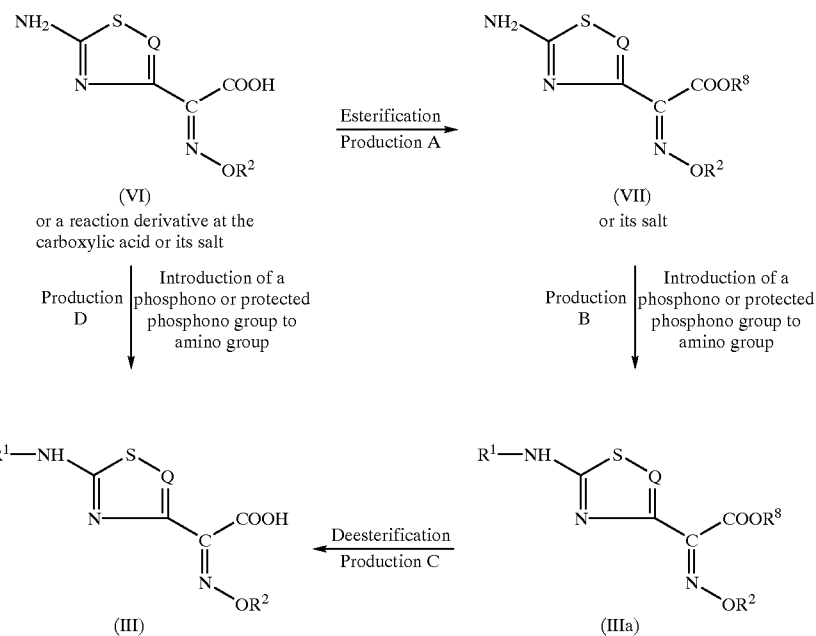

Production A

In the above formulas; $R^8$ is the ester part of the esterified carboxylic group represented by the formula: $CO_2R^8$.

A compound of the formula (VII) or salt (hereinafter referred to sometimes as Compound (VII)) can be produced by subjecting a compound of the formula (VI), its reactive derivative or its salt (hereinafter sometimes referred to as Compound (VI)) to esterification.

Examples of the preferable salts of Compound (VI) include, for example, a metal salt such as an alkali metal salt (e.g., sodium salt, potassium salt, etc.), an alkaline earth metal salt (e.g., calcium salt, magnesium salt, etc.), ammonium salt, an organic salt such as trimethylamine salt, triethylamine salt, pyridine salt, picoline salt, di-cyclohexylamine salt, N,N'-dibenzyl amine salt, etc., etc. Preferable examples of the reactive derivatives at carboxylic acid of Compound (VI) include those mentioned for Compound (III).

Examples of the esterifying agent used in the esterification reaction include a compound of the formula:

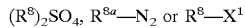

wherein $R^8$ has the meaning given above, $R^{8a}$ is a group removed a hydrogen atom from $R^8$, $X^1$ is hydroxy or a halogen.

Preferable examples of the halogen include chlorine, bromine, iodine and fluorine.

In case that a sulfuric acid ester and an alkyl halide are used as the esterifying agent, while the reaction is usually carried out in a solvent such as water, acetone, methylene chloride, ethanol, ether, dimethylformamide, etc., the reaction can be carried out in any solvent which does not interfere with the reaction. The reaction is preferably carried out in the presence of the inorganic base or the organic base mentioned above. The reaction temperature is not limiting but the reaction is usually carried out under cooling or under heating which is not higher than the boiling point of the solvent used.

In case that a diazo compound is used as the esterifying agent, the reaction is usually carried out in the presence of ether, tetrahydrofuran, etc., the reaction temperature is not limiting but the reaction is usually carried out under cooling or at an ambient temperature.

Preferable examples of the salts of Compound (VII) include, an acid addition salt such an organic acid salt as acetic acid salt, maleic acid salt, tartaric acid salt, benzenesulfonic acid salt, toluenesulfonic acid salt, etc., such inorganic acid salt as hydrochloric acid salt, hydrobromic acid salt, sulfuric acid salt, phosphoric acid salt, etc.

Productions B and D

A compound of the formula (III), its reactive derivatives at the carboxylic acid or its salt (hereinafter referred to as Compound (III)) and a compound of the formula (IIIa), its reactive derivatives at the carboxylic acid or its salt (hereinafter referred to as Compound (IIIa)) can be produced by introducing a phosphono group to the amino group of Compound (VI) and Compound (VII), respectively. Preferable examples of the reactive derivatives at the carboxylic acid of Compound (VI) and Compound (VII) include those mentioned for Compound (III).

Examples of the introducing agents to be used in the introduction reaction include, an phosphorus halide such as phosphorus trichloride, phosphorus pentachloride, etc., phosphorus oxychloride, etc. The reaction is usually carried out in a solvent such as a halogenated alkylene (e.g. methylene chloride, ethylene chloride, etc.) toluene, ethyl acetate, tetrahydrofuran, etc.

In this reaction, the reaction mixture containing Compound (III) or Compound (IIIa), wherein $R^1$ is a dihalophosphoryl group, which is obtained by reacting Compound (VI) or Compound (VI) with the above mentioned introducing agent such as a phosphorous halide, can be treated with water to give a reaction mixture containing Compound (III) or (IIIa) wherein $R^1$ is a phosphono group, or can treated with an alcohol such an alkanol as methanol, ethanol, etc. to give a reaction mixture containing Compound (III) or Compound (IIIa) wherein $R^0$ is an esterified phosphono group.

The reaction product (III) or (IIIa) wherein $R^0$ is a dihalophosphoryl group can be isolated from the above mentioned reaction mixture by means of a conventional isolation method. The product can be used in the following reaction.

The reaction includes changing Compound (IIIa) to the reactive derivative at the carboxylic group.

Production C

Compound (III) can be produced by subjecting Compound (IIIa) to deesterification reaction.

Preferable examples of the salt of Compound (III) include those enumerated for Compound (VI).

The reaction is carried out by a conventional method such as hydrolysis, reduction, etc. The hydrolysis is preferably carried out in the presence of a base or an acid. Preferable examples of the base include an inorganic base and an organic base such as an alkali metal (e.g. sodium, potassium, etc.), an alkaline earth metal (e.g. magnesium, calcium, etc.), hydroxide, carbonate, bicarbonate of the above mentioned metal, an trialkylamine (e.g. trimethylamine, triethylamine, etc.), picoline, 1,5-di-azabicyclo[4.3.0]nona-5-ene, 1,4-di-azabicyclo[2,2,2]octane, 1,8-di-azabicyclo[5.4.0]undecane, etc.

Preferable examples of the acid include an organic acid such as formic acid, acetic acid, propionic acid, trifluoroacetic acid, etc., an inorganic acid such as hydrochloric acid, hydrobromic acid, sulfuric acid, etc. Trifluoroacetic acid is preferably used in the presence of a -carbocation stabilizing agent such as anisole, etc.

While the reaction is usually carried out in water, methylene chloride, tetrahydrofuran, an alcohol (e.g. methanol, ethanol, etc.) or a mixture thereof, a solvent which does not interfere with the reaction may be used. A liquid base or an acid may also be used as a solvent. The reaction temperature is not limiting and the reaction is carried out usually under cooling or under mild conditions like slight heating.

The reduction can be applied to deprotection of a protecting group of the ester, such as 4-nitrobenzyl, 2-iodoethyl, 2,2,2-trichloro ethyl, etc. As the method of the reduction which is applied to the deesterification reaction, there may be mentioned a method using a metal such as zinc, zinc amalgam, etc., or a chromium compound salt such as chromous chloride salt, chromous acetate salt, etc., in combination with an organic or inorganic salt such as acetic acid, propionic acid, hydrochloric acid, etc., and a catalytic reduction method using a metal catalyst such as palladium-carbon, etc.

The production of a starting compound that is a compound of the formula (IIId) or its reactive derivative (hereinafter referred to as Compound (IIId)) is as follows.

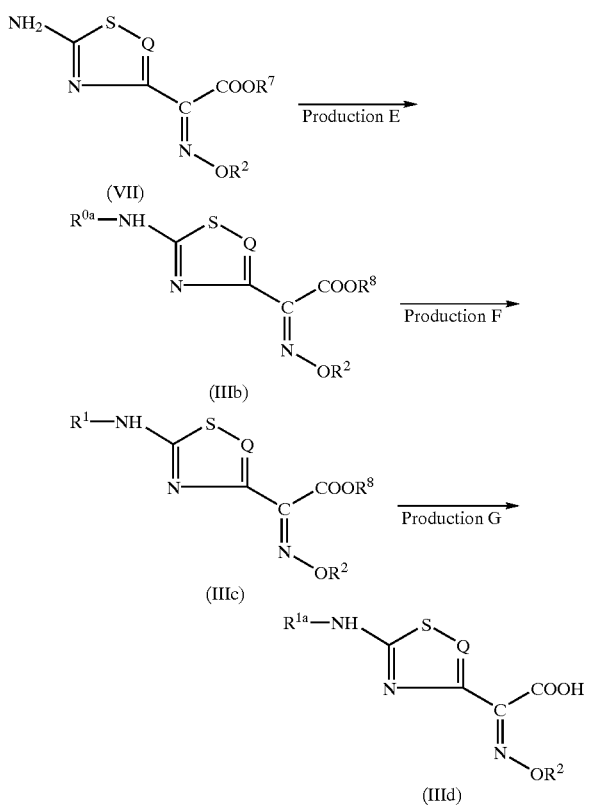

[wherein $R^{0a}$ is a dihalophosphoryl group, $R^{1a}$ is a phosphono group which may be protected. (The definition of $R^{1a}$ is the same as that of $R^1$, but $R^{1a}$ and $R^1$ may be the same as or different from each other.

Production E

A compound of the formula (IIIb), its reactive derivative or its salt (hereinafter referred to as Compound (IIIb)) can be produced by subjecting Compound (VII) to a reaction in which a dihalophosphoryl group is introduced to the amino group of Compound (VII). The reaction can be carried out in a similar manner to Production B or Production D.

Production F

A compound of the formula (IIIc), its reactive derivative or its salt (hereinafter referred to as Compound (IIIc)) can be produced by subjecting Compound (IIIb) to a reaction in which the dihalophosphoryl group is converted to a phosphono group other than dihalophosphoryl group. The reaction can be carried out by subjecting Compound (IIIb) to an esterification reaction and/or amidation reaction.

The esterification reaction is carried out by reacting Compound (IIIb) with an alcohol. Preferable examples of the alcohol include methanol, ethanol, propanol, butanol, etc. The amidation reaction can be carried out by reacting Compound (IIIb) with an amine. Preferable examples of the amine include ammonia, a primary amine such as methylamine, ethylamine, etc., a secondary amine such as morpholine, dimethylamine, etc., etc.

While the esterification reaction or amidation reaction is usually carried out in a solvent such as a halogenated alkylene (e.g. methylene chloride, ethylene chloride, etc.), tetrahydrofuran, water, etc., it can be carried out in any solvent which does not interfere with the reaction. The reaction temperature is not limiting though the reaction is carried out usually under cooling or an ambient temperature.

Production G

Compound (IIId) can be produced by subjecting Compound (IIIc) to deesterification reaction.

The reaction is carried out in a similar manner to that of Production C.

In the reactions mentioned above, when the starting compound has an amino group and/or a carboxyl group, these groups may be protected by a protecting group which is conventionally used in the field of peptide chemistry, and the protecting group may be removed after the reaction.

Examples of the protecting group for the amino group include, for example, a formyl group, a $C_{1-6}$alkyl-carbonyl group (for example, acetyl, ethylcarbonyl, etc.), a benzyl group, a tert-butyloxycarbonyl group, a benzyloxycarbonyl group, a 9-fluorenyl methyloxycarbonyl group, an allyloxycarbonyl group, a phenylcarbonyl group, a $C_{1-6}$alkyl-carbonyl group (for example, methoxycarbonyl, ethoxycarbonyl, etc.), a $C_{7-10}$aralkyl-carbonyl group (for example, benzylcarbonyl, etc.), a trityl group, phthaloyl group, a N,N-dimethylaminomethylene group, etc. These groups may be substituted by 1 to 3 of a halogen atom (for example, fluorine, chlorine, bromine, etc.), a nitro group, etc. Examples of the protecting group for the carboxyl group include, for example, a $C_{1-6}$alkyl group (for example, methyl, ethyl, propyl, isopropyl, butyl, tert-butyl, etc.), a phenyl group, a silyl group, a benzyl group, an allyl group, etc. These groups may be substituted by one to three of a halogen atom (for example, fluorine, chlorine, bromine, etc.), a nitro group, etc.

Examples of the protecting group for the hydroxy include, for example, a methoxy methyl group, an allyl group, a tert-butyl group, a $C_{7-10}$aralkyl group (for example, benzyl, etc.), formyl group, a $C_{1-6}$alkyl-carbonyl group (for example, acetyl, ethylcarbonyl, etc.), a benzoyl group, a $C_{7-10}$aralkyl-carbonyl group (for example, benzylcarbonyl, etc.), a pyranyl group, a furanyl group, a tri-alkyl silyl group, etc. These groups may be substituted by 1 to three of a halogen atom (for example, fluorine, chlorine, bromine, etc.), a $C_{1-6}$alkyl group (for example, methyl, ethyl, propyl, isopropyl, butyl, tert-butyl, etc.), a phenyl group, a $C_{7-10}$aralkyl group (for example, benzyl, etc.), a nitro group, etc.

As the method for the deprotection of these protecting group, a method using, for example, an acid, a base, reduction, ultraviolet ray, hydrazine, phenyl hydrazine, sodium N-methyl di-thiocarbamate, tetrabutyl ammonium fluoride, palladium acetate, etc. can be applied, using known or similar methods. When a compound is obtained as a free form in each reaction process, the compound can be converted to its salt, and when the compound is obtained as a salt, it can be converted to its free form or to an another salt.

Compound (I) thus obtained can be isolated from the reaction mixture and purified by a known procedure such as phase transfer, concentration, solvent extraction, fractional distillation, crystallization, recrystallization, chromatography, etc. When Compound (I) of the present invention exists in the form of diastereomer, conformer, etc., Compound (I) can be isolated and purified by a isolation procedure or a purification procedure mentioned above., if desirable. When Compound (I) is a racemate, (d)-form and (1)-form of Compound (I) can be isolated by a usual optical resolution procedure.

Compound (I) of the present invention has a solubility higher than that of the corresponding compound having an aminothiazolyl group wherein the amino group is free form (that is Compound (I) wherein $R^1$ is an amino group), and Compound (I) of the present invention in vivo, gives a corresponding compound having an aminothiazolyl group by removing group R¹. Further Compound (I) is superior in an anti-bacterial activity to a compound having aminothiazolyl group.

The compound (I) of this invention has broad spectrum antibacterial activity and low toxicity, and can be used safely for prophylaxis and therapy of various diseases, in man and mammals (e.g. mouse, rat, rabbit, dog, cat, cow and pig), caused by pathogenic bacteria, for example, respiratory infection and urinary tract infection. Characteristic features of the antibacterial spectrum of the antibacterial compound (I) are as follows, among others:

(1) showing a remarkably high activity against a variety of Gram-negative bacteria,
(2) having high activities against Gram-positive bacteria (e.g. *Staphylococcus aureus* and *Corynebacterium diphtheriae*),
(3) having high activities against methicillin-resistant *Staphylococcus aureus* (MRSA), and
(4) having high activities also against a number of β-lactamase-producing Gram-negative bacteria (e.g. genera Escherichia, Enterobacter, Serratia and Proteus).

The anti-bacterial compound (I) of the present invention has superior stability and effectiveness of anti-bacterial activity in comparison with Compound (V).

Though the drug of the present invention may comprise only Compound (I) itself, it is usually prepared by a conventional manner by using a proper amount of pharmaceutically acceptable carriers, diluents and bulking agents, etc. which are selected from exipients (for example, calcium carbonate, kaolin, sodium hydrogen carbonate, lactose, D-mannitol, starch, crystalline cellulose, talc, fine granulated sugar, porous substance, etc.), binders (for example, dextrin, gums, α-starch, gelatine, hydroxypropylcellulose, hydroxy propyl methyl cellulose, pullulan, etc.), thickeners (for example, a natural gum, a cellulose derivative, an acrylic acid derivative, etc.), disintegrators (for example, carboxymethylcellulose calcium, crosscarmelose sodium, crospovidone, a low-substituted hydroxypropylcellulose, partly pregelatinized starch, etc.), solvents (for example, water for injection, alcohol, propylene glycol, Macrogol, sesame oil, corn oil, etc.), dispersants (for example, Tween 80, HCO60, poly ethylene glycol, carboxymethylcellulose, sodium alginate, etc.), solubilizing agents (for example, polyethylene glycol, propylene glycol, D-mannitol, benzoic acid benzyl, ethanol, tris amino methane, triethanolamine, sodium carbonate, citric acid sodium, etc.), suspending agents (for example, stearyl triethanolamine, sodium lauryl sulfate, benzalkonium chloride, polyvinyllcohol, polyvinylpyrolidone, hydroxymethylcellulose, etc.), soothing agents (for example, benzyl alcohol, etc.), isotonic agents (for example, sodium chloride, glycerin, etc.), buffer agents (for example, phosphoric acid salt, acetic acid salt, carbonic acid salt, citric acid salt, etc.), lubricants (for example, magnesium stearate, calcium stearate, talc, starch, sodium benzoate, etc.), coloring agents (for example, tar pigment, caramel, ferric oxide, titanium oxide, riboflavins, etc.), corrigents (for example, a sweetining agent, a perfume, etc.), stabilizers (for example, sodium sulfite, ascorbic acid, etc.) and preservatives (for example, paraben, sorbic acid, etc.), etc.

The pharmaceutical composition of the present invention which may contain pharmaceutically acceptable carriers, diluents, bulking agents, etc., mentioned above contains an effective amount of Compound (I) of the present invention for the treatment and prevention of bacterial infectious disease. The amount of Compound (I) contained in the pharmaceutical preparation of the present invention is usually 0.1 to 100 weight % of the pharmaceutical preparation. The pharmaceutical preparation of the present invention may contain pharmaceutically active ingredients other than Compound (I)(e.g. antitumor agents, etc., mentioned below). The amount of the pharmaceutically active ingredient other than Compound (I) is not limited as long as the aim of the present invention can be achieved. Examples of the preparation includes tablets (including a sugar-coated tablet, a film-coated tablet), pills, capsules (including microcapsule), granules, fine granules, powders, drop infusions, syrups, emulsions, suspensions, injections, aerosols, ointments, suppositories, troches, cataplasms, sustained release preparations, etc. These preparations can be prepared by a conventional method (e.g., a method shown in The Pharmacopoeia of Japan The Twelfth Edition, etc.).

As carriers for injectable preparations, use is made of, for example, distilled water or a physiological saline solution. Carriers for capsules, powdery preparations, granular preparations or tablets are used as a mixture with known pharmaceutically acceptable excipients (e.g. starch, maltose, sucrose, calcium carbonate or calcium phosphate), binders (e.g. starch, gum arabic, carboxymethyl cellulose, hydroxypropyl cellulose or crystalline cellulose), lubricants (e.g. magnesium stearate or talc) and disintegrants (e.g. carboxymethyl calcium and talc).

The compound (I) of this invention can be administered, like known penicillin preparations or cephalosporin preparations, non-orally or orally as injectable preparations, capsules, tablets or granular preparations (injectable preparations are especially preferable). The daily dose ranges from 0.5 to 80 mg, preferably from 2 to 40 mg relative to 1 kg of the body weight of a man or an animal infected with pathogenic bacteria as described above, which may be administered in two to three divided doses.

Incidentally, the medicinal composition and antibacterial composition employed in the present specification may contain the compound (I) alone, or contain, among others, such carriers as set forth above, or contain a proper amount of any other adequate antibacterial compound.

The present invention will be illustrated in further detail in the following Working Examples, which are mere examples and do not limit this invention, and may be modified within the range not deviating from the scope of this invention.

Elutions in the column chromatography conducted in Working Examples were carried out while monitoring with TLC (Thin Layer Chromatography). In the TLC monitoring, as the TLC plate, use was made of 60F$_{254}$ manufactured by Merck & Co., Inc., as the developing solvent, use was made of the same solvent as employed for eluting in the column chromatography, and the detection was conducted with a UV detector. The silica gel (70 to 230 mesh) for the column was Kieselgel 60 manufactured by Merck & Co. Inc. ODS-AM is produced by YMC Co. Ltd., Dowex50W is produced by The Dow Chemical Company and Diaion HP-2OSS and SP-207 are produced by Mitsubishi Chemical Industries, Ltd.

NMR spectra were measured using tetramethylsilane as an internal or external standard with a spectrometer Gemini 200 and all delta values were expressed in ppm. The value shown in () for a mixed solvent is a mixing ratio in volume of constituent solvents. The percent (%) for a solution indicates the number of grams in 100 ml of the solution. And, the symbols in Reference Examples and Working Examples have the following meaning.

| | |
|---|---|
| s | : singlet |
| d | : doublet |
| t | : triplet |
| q | : quartet |
| ABq | : AB type quartet |
| dd | : double doublet |
| m | : multiplet |
| bs | : broad singlet |
| J | : coupling constant |

WORKING EXAMPLE 1

7β-[2(Z)-Ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate Under ice-cooling, the pH of a solution of 7β-amino-3-[4-(1-methyl-4-pyridinio)-2-thiazolylthio]-3-cephem-4-carboxylate hydrochloride (1.55 g) in a mixture of THF (50 ml) and $H_2O$ (50 ml) was adjusted to 7.4 with 0.6M $NaHCO_3$. To the solution was added portionwise 2-(5-dichlorophosphorylamino-1,2,4-thiadiazol-3-yl)-2(Z)-ethoxyiminoacetyl chloride (3.69 g), and the mixture was stirred at 5° C. for 10 minutes while maintaining the pH to 7.2 to 7.3 by addition of 0.6M $NaHCO_3$. A solution of sodium acetate (861 mg) in $H_2O$ (10 ml) was poured into the reaction mixture, and the resulting mixture was stirred at room temperature for 2.5 hours. During the stirring, the pH of the mixture was maintained above 4.5 by the occasional addition of 0.6M $NaHCO_3$ (total volume 56 ml). After the pH of the mixture was adjusted to 3.0 with 1N HCl (4 ml), the reaction mixture was concentrated under reduced pressure. The concentrate was diluted with $H_2O$ (800 ml) and purified by MCI gel HP-20SS column chromatography (500 ml: eluents=$H_2O$ 1.5L, 10% aq EtOH 0.5L, 20% aq EtOH 1.5L). The fractions containing the desired compound were concentrated under reduced pressure, and the concentrate was lyophilized to give the crude titled compound (1.64 g).

$^1$H NMR ($D_2O$) δ: 1.33 (3H,t,J=7.2 Hz), 3.56, 3.94 (2H,ABq,J=17.2 Hz), 4.34 (3H,s), 4.35 (2H,q,J=7.2 Hz), 5.38 (1H,d,J=5 Hz), 5.90 (1H,d,J=5 Hz), 8.34, 8.72 (each 2H,d,J=6.6 Hz), 8.51 (1H,s); IR (KBr, $cm^{-1}$): 3055, 1778, 1682, 1643, 1520, 1385, 1190, 1038.

WORKING EXAMPLE 2

7β-[2(Z)-Ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate The crude lyophilized compound (1.54 g) obtained in Working Example 1 was dissolved in a solution of $NaHCO_3$ (378 mg) in $H_2O$ (16 ml). The solution was subjected to ODS-AM column chromatography (450 ml: eluents=1N HCl 4.5 ml, $H_2O$ 0.1L, 5% aq acetonitrile 0.5L, 20% aq acetonitrile 0.25L). The fractions containing the desired compound were concentrated under reduced pressure, and the concentrate was lyophilized to give the titled compound (431 mg).

Anal Calcd for $C_{22}H_{21}N_8O_8PS_4 \cdot 2.0H_2O$: C, 36.66; H, 3.50; N, 15.55. Found: C, 36.70; H, 3.94; N, 15.53.

WORKING EXAMPLE 3

7β-[2(Z)-Fluoromethoxyimino-2-(5-phosphonoamino-1,2,4-thiadiazol-3-yl)acetamido]-3-[4-(1-methyl-4-pyridinio)-2-thiazolylthio]-3-cephem-4-carboxylate Under ice-cooling, the pH of a solution of 7β-amino-3-[4-(1-methyl-4-pyridinio)-2-thiazolylthio]-3-cephem-4-carboxylate hydrochloride (1.42 g) in a mixture of THF (50 ml) and $H_2O$ (50 ml) was adjusted to 7.5 with 0.6M $NaHCO_3$ (12 ml). To the solution was added portionwise 2-(5-dichlorophosphorylamino-1,2,4-thiadiazol-3-yl)-2(Z)-fluoromethoxyiminoacetyl chloride (3.41 g), and the mixture was stirred at 5° C. for 10 minutes while maintaining the pH to 7.2 to 7.5 by addition of 0.6M $NaHCO_3$ (24 ml). A solution of sodium acetate (787 mg) in $H_2O$ (20 ml) was poured into the reaction mixture, and the resulting mixture was stirred at room temperature for 3 hours. After the pH of the mixture was adjusted to 3.0 with 1N HCl (3.4 ml), the reaction mixture was concentrated under reduced pressure. The concentrate was diluted with $H_2O$ (750 ml) and purified by MCI gel HP-20SS column chromatography (500 ml: eluents=$H_2O$ 1.5L, 10% aq EtOH 0.5L, 20% aq EtOH1.5L). The fractions containing the desired compound were concentrated under reduced pressure, and the concentrate was lyophilized to give the crude titled compound (0.96 g).

$^1$H NMR ($D_2O$) δ: 3.57, 3.94 (2H,ABq,J=17.4 Hz), 4.34 (3H,s), 5.40 (1H,d,J=4.8 Hz), 5.85 (2H,d,J=55 Hz), 5.93 (1H,d,J=4.8 Hz), 8.34, 8.72 (each 2H,d,J=6.4 Hz), 8.51 (1H,s); IR (KBr, $cm^{-1}$): 3055, 1781, 1677, 1642, 1523, 1364, 1189, 1071.

WORKING EXAMPLE 4

7β-[2(Z)-Fluoromethoxyimino-2-(5-phosphonoamino-1,2,4-thiadiazol-3-yl)acetamido]-3-[4-(1-methyl-4-pyridinio)-2-thiazolylthio]-3-cephem-4-carboxylate The crude lyophilized compound (0.96 g) obtained in Working Example 3 was dissolved in a solution of $NaHCO_3$ (234 mg) in $H_2O$ (15 ml). The solution was subjected to ODS-AM column chromatography (450 ml: eluents=1N HCl 3.06 ml, $H_2O$ 1.0L, 20% aq acetonitrile 0.25L, 30% aq acetonitrile 0.6L). The fractions containing the desired compound were concentrated under reduced pressure, and the concentrate was lyophilized to give the titled compound (600 mg).

Anal Calcd for $C_{21}H_{18}N_8O_8FPS_4 \cdot 2.0H_2O$: C, 34.81; H, 3.06; N, 15.46; P, 4.27. Found: C, 34.84; H, 3.28; N, 15.43; P, 4.18.

WORKING EXAMPLE 5

7β-[2(Z)-Ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate Under ice-cooling, 0.6M $NaHCO_3$ (34 ml) was added to a solution of 7β-amino-3-[4-(1-methyl-4-pyridinio)-2-thiazolylthio]-3-cephem-4-carboxylate hydrochloride (3.0 g) in a mixture of THF (150 ml) and $H_2O$ (150 ml). To the solution were added portionwise 2-(5-dichlorophosphorylamino-1,2,4-thiadiazol-3-yl)-2(Z)-ethoxyiminoacetyl chloride (4.76 g) and 0.6M $NaHCO_3$ (23 ml) successively. The resulting mixture was stirred at 5° C. for 15 minutes and then at room temperature for 2 hours. Under ice-cooling, the pH of the reaction mixture was adjusted to 5.0 with 1N NaOH, and the mixture was concentrated under reduced pressure. The concentrate was diluted with $H_2O$ (2.5L), and the pH of the solution was adjusted to 3.0with 1N HCl. The mixture was purified by MCI gel SP-207 column chromatography (750 ml: eluents=$H_2O$ 4L, 15% aq EtOH 6L). The fractions containing the desired compound were concentrated under reduced pressure, and the concentrate was lyophilized to give the crude titled compound (2.6 g).

$^1$H NMR (DMSO-d$_6$) δ: 1.23 (3H,t,J=7 Hz), 3.56, 3.94 (2H,ABq,J=17 Hz), 4.17 (2H,q,J=7 Hz), 4.33 (3H,s), 5.30 (1H,d,J=5 Hz), 5.90 (1H,dd,J=5&8.8 Hz), 8.50, 8.97 (each 2H,d,J=6.4 Hz), 8.98 (1H,s), 9.22 (1H,m), 9.69 (1H,d,J=8.8 Hz).

WORKING EXAMPLE 6

7β-[2(Z)-Ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate The crude lyophilized compound (1.24 g) obtained in Working Example 5 was dissolved in H$_2$O (13 ml) containing 1N NaOH (3.24 ml). The solution was subjected to ODS-AM column chromatography (450 ml: eluents=H$_2$O). The fractions containing sodium salt form of the desired compound were passed through Dowex 50×8 column (H form, 20 to 50 mesh, 100 ml). The eluent was concentrated under reduced pressure, and the concentrate was lyophilized to give the titled compound (377 mg).

Anal Calcd for C$_{22}$H$_{21}$N$_8$O$_8$PS$_4$·3.5H$_2$O: C, 35.29; H, 3.77; N, 14.97. Found: C, 35.26; H, 3.45; N, 14.99. $^1$H NMR (DMSO-d$_6$) δ: 1.24 (3H,t,J=7 Hz), 3.54, 3.94 (2H,ABq,J=17 Hz), 4.20 (2H,q,J=7 Hz), 4.33 (3H,s), 5.30 (1H,d,J=5.2 Hz), 5.89 (1H,dd,J=5.2&8.6 Hz), 8.51, 8.98 (each 2H,d,J=5.6 Hz), 8.98 (1H,s), 9.17 (1H,m), 9.69 (1H,d,J=8.6 Hz).

WORKING EXAMPLE 7

7β-[2(Z)-Ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate Trimethylsilylacetamide (919 mg) was added to a suspension of 7β-amino-3-[4-(1-methyl-4-pyridinio)-2-thiazolylthio]-3-cephem- 4-carboxylate hydrochloride (240 mg) in dichloromethane (4 ml), and the mixture was stirred at room temperature for 40 minutes. To the mixture was added portionwise 2-(5-dichlorophosphorylamino-1,2,4-thiadiazol-3-yl)-2(Z)-ethoxyiminoacetyl chloride (351 mg) under cooling at −15° C., and the mixture was stirred at −15 to −5° C. for 1 hour. After concentration of the reaction mixture under reduced pressure, the concentrate was diluted with H$_2$O (150 ml). Under ice-cooling, the pH of the mixture was adjusted to 5.0 with 1N NaOH. The mixture was diluted with H$_2$O (200 ml), and the pH of the mixture was adjusted to 3.0 with 1N HCl. The mixture was purified by MCI gel SP-207 column chromatography (180 ml: eluents=H$_2$O 0.5L, 15% aq EtOH 0.6L). The fractions containing the desired compound were concentrated under reduced pressure, and the concentrate was lyophilized to give the crude titled compound (100 mg).

$^1$H NMR (DMSO-d$_6$) δ: 1.23 (3H,t,J=7 Hz), 3.56, 3.94 (2H,ABq,J=17 Hz), 4.17 (2H,q,J=7 Hz), 4.33 (3H,s), 5.30 (1H,d,J=5 Hz), 5.90 (1H,dd,J=5&8.8 Hz), 8.50, 8.97 (each 2H,d,J=6.4 Hz), 8.98 (1H,s), 9.22 (1H,m), 9.69 (1H,d,J=8.8 Hz).

WORKING EXAMPLE 8

The lyophilized 7β-[2(Z)-ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate (300 mg equivalent), obtained in Working Example 6, was dissolved in saline, the pH was adjusted to 6.0, and saline was added to make the total volume 5 ml (60 mg equivalent/ml).

Experiment 1

The lyophilized 7β-[2(Z)-ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate obtained in Working Example 6, was dissolved in mouse plasma to prepare 10 mg equivalent/ml solution. After incubation at 37° C., the transformation rate into 7β-[2(Z)-ethoxyimino-2-(5-amino-1,2,4-thiadiazol-3-yl) acetamido]-3-[4-(1-methyl-4-pyridinio)-2-thiazolylthio]-3-cephem-4-carboxylate (amino form) was measured. The transformation rates in 30 minutes and 1 hour were as follows:

30 minutes 35%

1 hour 62%

INDUSTRIAL APPLICABILITY

The cephem compound (I) has a broad antibacterial spectrum and an excellent antibacterial activity against Gram-negative bacteria and Gram-positive bacteria including *Staphylococcus aureus* and MRSA, and is useful for treatment or prevention of infectious diseases caused by these bacteria. Additionally, the compound (I) has a relatively high solubility in water, and can be advantageously used for injection.

What is claimed is:

1. A compound of the formula:

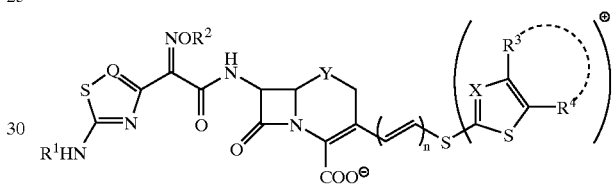

wherein $R^1$ is a phosphono group;

$R^2$ is a hydrogen atom, an optionally substituted $C_{1-6}$ alkyl group or a $C_{3-5}$ cycloalkyl group;

each of Q and X is a nitrogen atom or CH;

Y is S;

n is 0 or 1;

one of $R^3$ and $R^4$ is a pyridinium group which may be substituted and the other is a hydrogen atom or a hydrocarbon group which may be substituted, or $R^3$ and $R^4$ taken together may form a quaternized nitrogen-containing heterocyclic ring which may be substituted, wherein when $R^3$ and $R^4$ are taken together, the group of the formula

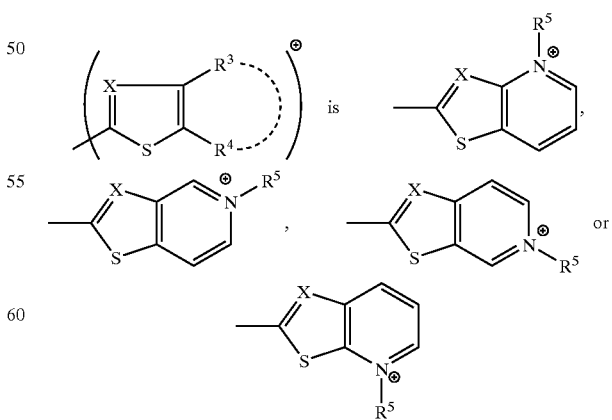

wherein $R^5$ is an optionally substituted hydrocarbon group; or salt thereof.

2. 7β-[2(Z)-ethoxyimino-2-(5-phosphonoamino-1,2,4-thiadiazole-3-yl)acetamido]-3-[4-(1-methyl-4-pyridinio)-2-thiazolylthio]-3-cephem-4-carboxylate.

3. A method for producing a pharmaceutical composition comprising
   mixing a compound of claim 1 with a pharmaceutically acceptable carrier, diluent or bulking agent.

4. 7β-[2(Z)-ethoxyimino-2-(5-phosphonoamino 1,2,4-thiadiazole-3-yl)acetamido]-3-[4-(1-methyl-4-pyridinio)-2-thiazolylthio]-3-cephem-4-carboxylate or its salt.

5. A method for treating a bacterial infection which comprises administering an effective amount of a compound as claimed in claim 1 to a patient suffering from the bacterial infection.

6. A method for treating a bacterial infection which comprises administering an effective amount of a compound as claimed in claim 1 together with at least one of pharmaceutically acceptable carriers, diluents and excipients to a patient suffering from the bacterial infection.

7. A method as claimed in claim 5, wherein the bacterial infection is a MRSA infection.

8. A compound as claimed in claim 1, wherein $R^3$ is a pyridinium group which may be substituted and $R^4$ is a hydrogen atom.

9. A compound as claimed in claim 1, wherein Q is a nitrogen atom.

10. A compound as claimed in claim 1, wherein X is a nitrogen atom.

11. A compound as claimed in claim 1, wherein n is 0.

12. A method for treating a bacterial infection which comprises administering an effective amount of a compound as claimed in claim 4 to a patient suffering from the bacterial infection.

13. A compound as claimed in claim 1, which is 7β-[2(Z)-fluoromethoxyimino-2-(5phophonoamino-1,2,4-thiadiazole-3-yl)acetamido]-3-[4-(1-methyl-4-pyridinio)-2-thiazolylthio]-3-cephem-4carboxylate or its salt.

14. A method for producing a compound as claimed in claim 1, which comprises reacting a compound of the formula:

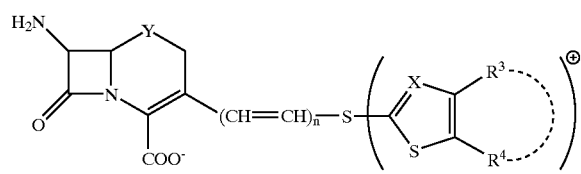

or its salt;
   wherein each symbol has the meaning given in claim 1;
   with a compound of the formula:

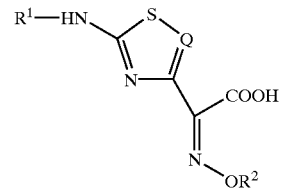

its salt or its reactive derivative;
   wherein each symbol has the meaning given in claim 1.

15. A method as claimed in claim 5, wherein the compound is administered by injection.

16. A method for treating a bacterial infection which comprises administering an effective amount of a compound as claimed in claim 4 together with at least one of pharmaceutically acceptable carriers, diluents and excipients to a patient suffering from the bacterial infection.

17. A pharmaceutical composition containing the compound shown in claim 1 and at least one of pharmaceutically acceptable carriers, diluents and bulking agents.

18. A pharmaceutical composition containing the compound of claim 4 and at least one of pharmaceutically acceptable carriers, diluents and bulking agents.

19. A method for producing a pharmaceutical composition comprising mixing a compound of claim 4 with a pharmaceutically acceptable carrier, diluent or bulking agent.

20. A method as claimed in claim 12, wherein the compound is administered by injection.

21. A method as claimed in claim 12, wherein the bacterial infection is a MRSA infection.

* * * * *